(12) United States Patent
Maa et al.

(10) Patent No.: US 11,191,863 B2
(45) Date of Patent: Dec. 7, 2021

(54) ANTIVIRAL AIR-FILTERING LIGHTING DEVICE USING VISIBLE LIGHT

(71) Applicant: Aleddra Inc., Renton, WA (US)

(72) Inventors: Chia-Yiu Maa, Bellevue, WA (US); Chun-Te Yu, Bellevue, WA (US)

(73) Assignee: Aleddra Inc., Renton, WA (US)

(*) Notice: Subject to any disclaimer, the term of this patent is extended or adjusted under 35 U.S.C. 154(b) by 0 days.

(21) Appl. No.: 17/148,277

(22) Filed: Jan. 13, 2021

(65) Prior Publication Data

US 2021/0128774 A1  May 6, 2021

Related U.S. Application Data

(63) Continuation-in-part of application No. 17/094,567, filed on Nov. 10, 2020, now Pat. No. 11,103,612, which is a continuation-in-part of application No. 16/180,416, filed on Nov. 5, 2018, now Pat. No. 10,874,762.

(51) Int. Cl.
  *A61L 9/18* (2006.01)
  *A61L 9/16* (2006.01)

(52) U.S. Cl.
  CPC ............... *A61L 9/18* (2013.01); *A61L 9/16* (2013.01); *A61L 2209/11* (2013.01); *A61L 2209/12* (2013.01); *A61L 2209/14* (2013.01); *A61L 2209/21* (2013.01)

(58) Field of Classification Search
  CPC .......... A61L 9/16; A61L 9/18; A61L 2209/11; A61L 2209/12; A61L 2209/14; A61L 2209/21; B01J 19/127; B01J 21/063; B01J 21/004
  See application file for complete search history.

(56) References Cited

U.S. PATENT DOCUMENTS 8,746,929 B2 * 6/2014 Budai ............... F21V 33/00
                                                    362/253
8,900,518 B2 * 12/2014 Seck ................ F21V 1/00
                                                    422/121

* cited by examiner

*Primary Examiner* — Lessanework Seifu
(74) *Attorney, Agent, or Firm* — Han IP PLLC; Andy M. Han

(57) ABSTRACT

An antiviral air-filtering lighting device includes an air-permeable lampshade, a visible light source, a driver, and an air circulation mechanism. The lampshade diffuses a visible light emitted from the visible light source and includes an air inlet port. The lampshade is coated with a visible-light activatable antiviral photocatalytic coating. The visible light source is disposed inside the lampshade to shine its light through the lampshade to activate the visible-light activatable antiviral photocatalytic coating on the lampshade. The air circulation mechanism sucks an ambient air from outside the lighting device, and forces the air through the lampshade. The lampshade traps airborne microbials on the surface having the visible-light activatable antiviral photocatalytic coating. A light emitted by the first visible light source activates a photocatalyst material in the visible-light activatable antiviral photocatalytic coating, and the airborne microbials trapped by the air filter are killed or deactivated by the activated photocatalyst material.

11 Claims, 2 Drawing Sheets

ANTIVIRAL AIR-FILTERING LIGHTING DEVICE USING VISIBLE LIGHT

CROSS REFERENCE TO RELATED PATENT APPLICATIONS

The present disclosure is a continuation-in-part (CIP) of U.S. patent application Ser. No. 17/094,567, filed 10 Nov. 2020, which is a CIP of U.S. patent application Ser. No. 16/180,416, filed 5 Nov. 2018 and issued as U.S. Pat. No. 10,874,762 on 29 Dec. 2020, the contents of which being incorporated by reference in their entirety.

BACKGROUND

Technical Field

The present disclosure pertains to the field of lighting devices and, more specifically, proposes an antiviral air-filtering lighting device.

Description of Related Art

In U.S. patent application Ser. No. 16/180,416, an air-filtering anti-bacterial lighting apparatus was introduced. That lighting apparatus comprises one translucent housing, at least one light source, and an air circulation mechanism. The translucent housing may be air-permeable, and it includes at least one air-inflow port. A surface of the translucent housing is coated with anti-bacterial photocatalytic film. The at least one lighting source is disposed inside the housing. The light originated from the light source shines through the translucent housing, thus illuminating the area around the apparatus. The light also activates the anti-bacterial photocatalytic film on the housing so that it would kill pathogens making contact with it. The air circulation inside the housing sucks the ambient air from outside the housing and forces the air through the air-permeable housing. As the air passing through, the air-permeable housing traps airborne pathogens, and the activated anti-bacterial photocatalytic film would kill the trapped pathogens.

The teaching of U.S. patent application Ser. No. 16/180,416 lays a good foundation for an air-filtering anti-bacterial lighting apparatus. In the present disclosure, the inventors of U.S. patent application Ser. No. 16/180,416 will expand that teaching by adding new conditions for enhancing the practicality and the usefulness of such air-filtering anti-bacterial lighting device.

SUMMARY

In one aspect, the lighting device comprises a lampshade with an interior surface and an exterior surface, a first visible light source emitting a light in a wavelength rang of 400~700 nm, a driver, and an air circulation mechanism. The driver converts an external power to an internal power to activate either the first visible light source or the air circulation mechanism or both. The driver plays a critical role in enhancing the functionality of the lighting device as will be seen later. The lampshade diffuses the visible light emitted by the first visible light source and includes an air inlet port. The lampshade is air-permeable and is coated with a visible-light activatable antiviral photocatalytic coating on at least one of the interior surface and the exterior surface. The first visible light source is disposed inside the lampshade, and its light shines through the lampshade and activates the visible-light activatable antiviral photocatalytic coating on the lampshade. The air circulation mechanism is disposed near the air inlet port of the lampshade, sucks an ambient air from outside the lighting device, and forces the air through the air-permeable lampshade. The lampshade traps airborne microbials carried in the air on the surface having the visible-light activatable antiviral photocatalytic coating thereof. The light emitted by the first visible light source activates a photocatalyst material in the visible-light activatable antiviral photocatalytic coating. Moreover, the airborne microbials trapped by the lampshade are killed or deactivated by the activated photocatalyst material. The lampshade serves four distinct functions: (1) as a housing to house the first visible light source, (2) as a diffuser to soften the light emitted by the first visible light source, (3) as an air filter to filter airborne microbials, and (4) as a visible-light activatable photocatalytic medium to kill airborne microbials through the antiviral photocatalytic coating on its surface. Finally, the lighting device includes neither ultraviolet (UV) light source nor infrared (IR) light source. This is to ensure the lighting device will not emit any UV or IR light since the lighting device may be used as a desktop lamp next to a user for a long duration, thus preventing any potential of a long exposure of a UV or IR light to a user. This is an important restriction on the present disclosure and is not addressed in U.S. patent application Ser. No. 16/180,416.

In some embodiments, the lampshade requires no frame to house the first visible light source. The lampshade can support its own structure without any additional frame internally or externally.

As stated earlier, the lampshade does not contain or otherwise require any frame to house the first visible light source. However, under some situation, it may be beneficial to have an external housing to protect the lampshade from damage. Thus, in some embodiments, the present disclosure further comprises a housing to house the lampshade and the air circulation mechanism, and there are openings on the housing for the air to exit out of the lighting device.

In some embodiments, the visible-light activatable antiviral photocatalytic coating on the lampshade contains titanium oxide ($TiO_2$). In some other embodiments, the visible-light activatable antiviral photocatalytic coating on the lampshade contains titanium oxide ($TiO_2$) as a primary photocatalyst, and an active metal ingredient as the secondary photocatalyst, and wherein the active metal ingredient comprises silver, gold, copper, zinc, nickel, or a combination thereof. These metals when embedded in the photocatalyst are known to enhance the photocatalytic activity with visible light. Some photocatalytic coating may contain more than one type of metals for a better photocatalytic effectiveness.

In some embodiments, the air circulation mechanism is a fan. It is foreseeable to have more than one fans to increase the airflow.

In some embodiments, the driver is configured to dim the light output of the first light source. The driver may be configured to support bi-level dimming, step dimming (e.g., 25%, 50%, 75%, 100%) or liner dimming.

The speed of the fan is proportional to the noise level. When using the present disclosure as a desktop lamp, it may be desirable to reduce the noise level by lowering the fan speed. Therefore, on some embodiments, the driver is configured to change the speed of the fan.

In some embodiments, the first light source comprises one more light emitting diodes (LEDs) each emitting the visible light.

In some embodiments, the first visible light source further comprises a second visible light source and a third visible light source, wherein a color temperature of the second visible light source is higher than a color temperature of the third visible light source. A light source with a higher color temperature tends to provide a stronger circadian stimulus and is thus suitable for daytime use. In comparison, a light source with a lower color temperature tends to provide a lesser circadian stimulus and is thus suitable for nighttime use. By having both color temperatures available, the present disclosure afford the user to choose a color temperature according to the circadian stimulus the user wants to receive.

In some embodiment, the present disclosure further comprises a controller, where the controller is configured to tune a color temperature of the first visible light source by mixing a combination ratio of the color temperatures of the second visible light source and the third visible light source, either manually or automatically according to a circadian schedule stored in a memory module of the controller. With this functionality, rather than picking between only two color temperatures (from the second light source and the third light source), the user may now be able to select any color temperature between the color temperature of the second light source and the color temperature of the third light source.

BRIEF DESCRIPTION OF THE DRAWINGS

The accompanying drawings are included to aid further understanding of the present disclosure, and are incorporated in and constitute a part of the present disclosure. The drawings illustrate a select number of embodiments of the present disclosure and, together with the detailed description below, serve to explain the principles of the present disclosure. It is appreciable that the drawings are not necessarily to scale, as some components may be shown to be out of proportion to size in actual implementation in order to clearly illustrate the concept of the present disclosure.

DETAILED DESCRIPTION OF PREFERRED EMBODIMENTS

Overview

Various implementations of the present disclosure and related inventive concepts are described below. It should be acknowledged, however, that the present disclosure is not limited to any particular manner of implementation, and that the various embodiments discussed explicitly herein are primarily for purposes of illustration. For example, the various concepts discussed herein may be suitably implemented in a variety of lighting devices having different form factors.

The present disclosure discloses an antiviral air-filtering lighting device includes a lampshade, a visible light source, a driver, and an air circulation mechanism such as a fan. The lampshade diffuses the visible light emitted from the visible light source and includes an air inlet port. Moreover, the lampshade is air-permeable and is coated with a visible-light activatable antiviral photocatalytic coating on a surface. The visible light source is disposed inside the lampshade, and its light shines through the lampshade and activates the visible-light activatable antiviral photocatalytic coating on the lampshade. The air circulation mechanism is disposed near the air inlet port of the lampshade, sucks an ambient air from outside the lighting device, and forces the air through the lampshade. The lampshade traps airborne microbials on the surface having the visible-light activatable antiviral photocatalytic coating. A light emitted by the first visible light source activates a photocatalyst material in the visible-light activatable antiviral photocatalytic coating, and the airborne microbials trapped by the lampshade, which functions as an air filter, are killed or deactivated by the activated photocatalyst material.

Example Implementations

Figure 1:
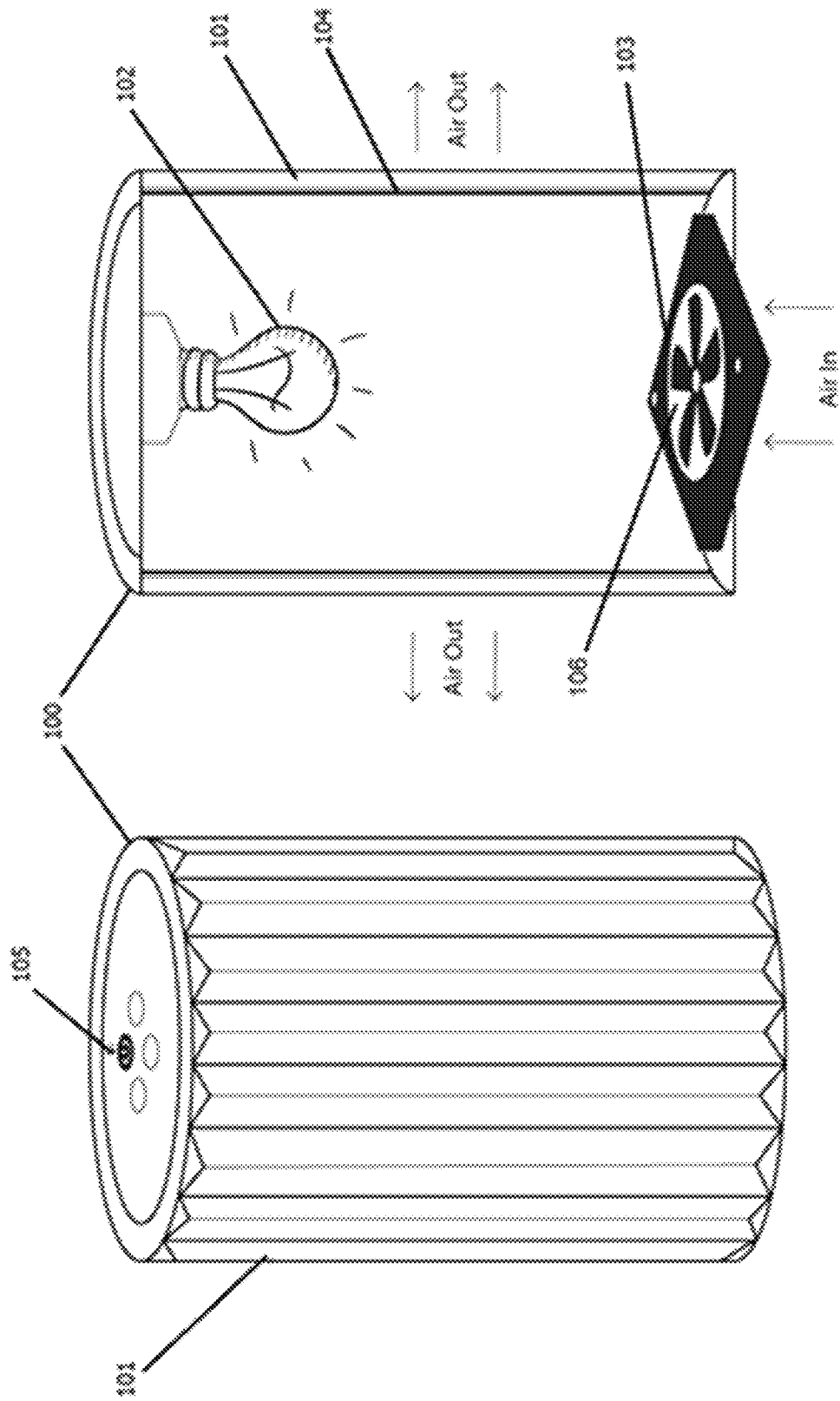
FIG. 1 schematically depicts a diagram of an antiviral air-filtering desktop lighting fixture with a light bulb.

FIG. 1 is an embodiment of the lighting device of the present disclosure in a form of a desktop lighting fixture 100. The light source 102 is a regular light bulb and is disposed inside the lampshade 101. The light source 102 emits visible light, and the lighting fixture 100 includes neither UV light source nor IR light source. The lampshade 101 has an interior surface and an exterior surface, diffuses the light emitted from the light source 102, and is air-permeable. The lampshade 101 is frameless as it requires no frame to house the light source 102. The air circulation mechanism is a fan 103 located at the air inlet port 106 of the lampshade 101. The other end of the lampshade is covered with a control panel 105 for turning on and off the light source 102 and the fan 103. The interior surface of the lampshade 101 is coated with a visible-light activatable photocatalytic coating 104 comprising a primary photocatalyst material $TiO_2$ and a secondary photocatalyst material, nano silver. The photocatalyst materials in the photocatalytic coating 104 are activated by a light emitted by the light source 102. The ambient air is pulled into the lampshade through the fan 103 and then passes through the photocatalytic coating 104 and finally exits out of the lighting fixture through the air-permeable lampshade 101. The airborne pathogens are trapped by the air-permeable lampshade 101 and killed by an activated photocatalyst material in the photocatalytic coating 104. The lampshade 101 has a folding surface for increasing the overall surface area and efficiency of air filtering and antiviral photocatalytic killing. The air-permeable lampshade is made of non-woven fabric. Though not shown in the figure, the control panel 105 can be removed for replacing the light source 102 and the lampshade 101. Also not shown in the figure is a driver that converts external 110V AC power to 24V DC for driving the fan 103. The light bulb 102 is AC-driven and does not need a driver in this embodiment.

Figure 2:
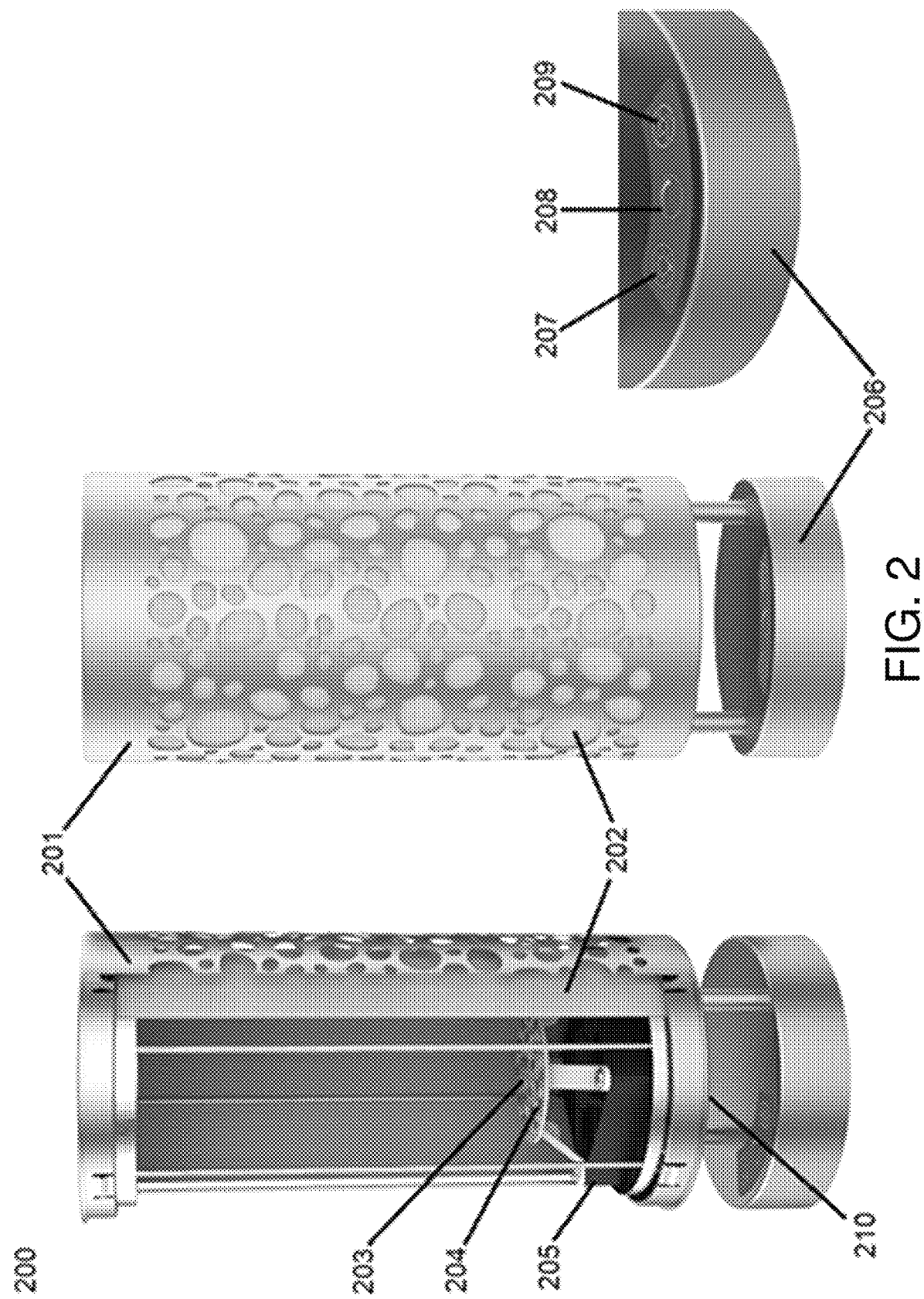
FIG. 2 schematically depicts images of an antiviral air-filtering desktop lighting fixture with LEDs.

FIG. 2 is another embodiment of the lighting device of the present disclosure in a form of a desktop lighting fixture 200. The fixture 200 has an external housing 201 to house the lampshade 202 and the fan 205. There are openings on the external housing 201 for the air to pass through. The fan 205 is disposed at the air inlet port 210 of the lampshade. The lampshade diffuses the light emitted by two types of visible light LEDs 203, 204. The lampshade 202 is made of non-woven fabric and is coated with a visible-light activatable photocatalytic coating (though not shown) on both interior and exterior surfaces. The LED light source 203 has a higher color temperature at 5000K and the LED light source 204 has a lower color temperature at 2700K. The lighting fixture 200 includes neither UV light source nor IR light source. A driver and a controller are hidden inside the base 206 of the fixture 200. Through the touch button 207, the controller can switch among three color temperatures: 2700K, 3850K, and 5000K. The controller mixes 2700K LEDs and 5000K LEDs each at 50% light output to create 3850K color temperature. Through the touch button 206, the driver allows a user to perform a bi-level dimming (50% and 100%) on the LED light sources 203, 204. Through the touch button 209, the driver let the user to change the speed of the fan 205. A light emitted by the LED light sources 203, 204 activates the visible-light activatable photocatalytic coating on the lampshade 202. The ambient air is pulled into the lampshade by the fan 205 through the air inlet 210 and then exit out the lighting fixture through the air-permeable lampshade 202 and the external housing 201. The airborne pathogens are trapped by the lampshade 202 and killed by an activated photocatalyst material in the photocatalytic coating on the lampshade 202.

Additional and Alternative Implementation Notes

Although the techniques have been described in language specific to certain applications, it is to be understood that the appended claims are not necessarily limited to the specific features or applications described herein. Rather, the specific features and examples are disclosed as non-limiting exemplary forms of implementing such techniques.

As used in this application, the term "or" is intended to mean an inclusive "or" rather than an exclusive "or." That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more," unless specified otherwise or clear from context to be directed to a singular form.

What is claimed is:

1. A lighting device, comprising:
   a lampshade with an interior surface and an exterior surface;
   a first visible light source configured to emit a visible light in a wavelength range of 400~700 nm;
   a driver; and
   an air circulation mechanism,
   wherein, in operation:
      the driver converts an external power to an internal power to activate either or both of the first visible light source and the air circulation mechanism,
      the lampshade diffuses the visible light emitted from the first visible light source,
      the lampshade comprises an air inlet port,
      the lampshade is air-permeable and is coated with a visible-light activatable antiviral photocatalytic coating on at least one of the interior surface and the exterior surface,
      the first visible light source is disposed inside the lampshade and its light shines through the lampshade to activate the visible-light activatable antiviral photocatalytic coating on the lampshade,
      the air circulation mechanism is disposed near the air inlet port of the lampshade and sucks an ambient air from outside the lighting device to force the air through the air-permeable lampshade,
      the lampshade traps airborne microbials carried in the air on the at least one of the interior surface and the exterior surface having the visible-light activatable antiviral photocatalytic coating thereof,
      the visible light emitted by the first visible light source activates a photocatalyst material in the visible-light activatable antiviral photocatalytic coating,
      the airborne microbials trapped by the lampshade are killed or deactivated by the activated photocatalyst material, and
      the lighting device comprises no ultraviolet (UV) light source or infrared (IR) light source.

2. The lighting device of claim 1, wherein the lampshade requires no frame to house the first visible light source.

3. The lighting device of claim 1, further comprising:
   a housing configured to house the lampshade and the air circulation mechanism, the housing having openings thereon to allow the air to exit out of the lighting device.

4. The lighting device of claim 1, wherein the visible-light activatable antiviral photocatalytic coating on the lampshade contains titanium oxide ($TiO_2$).

5. The lighting device of claim 1, wherein the visible-light activatable antiviral photocatalytic coating on the lampshade contains titanium oxide ($TiO_2$) as a primary photocatalyst and an active metal ingredient as the secondary photocatalyst, and wherein the active metal ingredient comprises silver, gold, copper, zinc, nickel, or a combination thereof.

6. The lighting device of claim 1, wherein the air circulation mechanism comprises a fan.

7. The lighting device of claim 6, wherein the driver is configured to change a speed of the fan.

8. The lighting device of claim 1, wherein the first light source comprises one more light emitting diodes (LEDs) each emitting the visible light.

9. The lighting device of claim 1, wherein the driver is configured to dim a light output of the first light source.

10. The lighting device of claim 1, wherein the first visible light source comprises a second visible light source and a third visible light source, and wherein a color temperature of the second visible light source is higher than a color temperature of the third visible light source.

11. The lighting device of claim 10, further comprising:
    a controller,
    wherein the controller is configured to tune a color temperature of the first visible light source by mixing a combination ratio of the color temperatures of the second visible light source and the third visible light source, either manually or automatically, according to a circadian schedule stored in a memory module of the controller.

* * * * *